United States Patent [19]

Barabino et al.

[11] Patent Number: 4,781,712

[45] Date of Patent: Nov. 1, 1988

[54] FEMININE PAD WITH ATTACHED DISPOSAL WRAP

[75] Inventors: William A. Barabino, North Reading; Raymond S. Dean, Lynn, both of Mass.

[73] Assignee: Personal Hygiene Research Associates, North Reading, Mass.

[21] Appl. No.: 37,198

[22] Filed: Apr. 10, 1987

[51] Int. Cl.[4] .............................................. A61F 13/16
[52] U.S. Cl. .................................................. 604/385.1
[58] Field of Search ...................... 604/385.1, 358, 386, 604/387

[56] References Cited

U.S. PATENT DOCUMENTS 3,970,087  7/1976  Castaneda ........................... 604/387
4,285,343  8/1981  McNair ............................... 604/387
4,402,689  9/1983  Baum .................................. 604/387
4,608,047  8/1986  Mattingly .......................... 604/387

Primary Examiner—John D. Yasko
Attorney, Agent, or Firm—Richard C. Litman

[57] ABSTRACT

An absorbent napkin with infolding wrap consisting of an absorbent pad of elongated rectangular configuration with elongate edges defining a short and long dimension and having a body face and an outer face for engagement to clothing, a wrap member attached to at least one of the several elongated edges and adapted to fold along the one of the elongate edges of the members to inwrap the body face, and an adhesive member secured transversely of the wrap member for adhesive engagement to the clothing. The wrap members along the longer dimension are at least half-lengths of the long dimension of the absorbent pad.

11 Claims, 5 Drawing Sheets

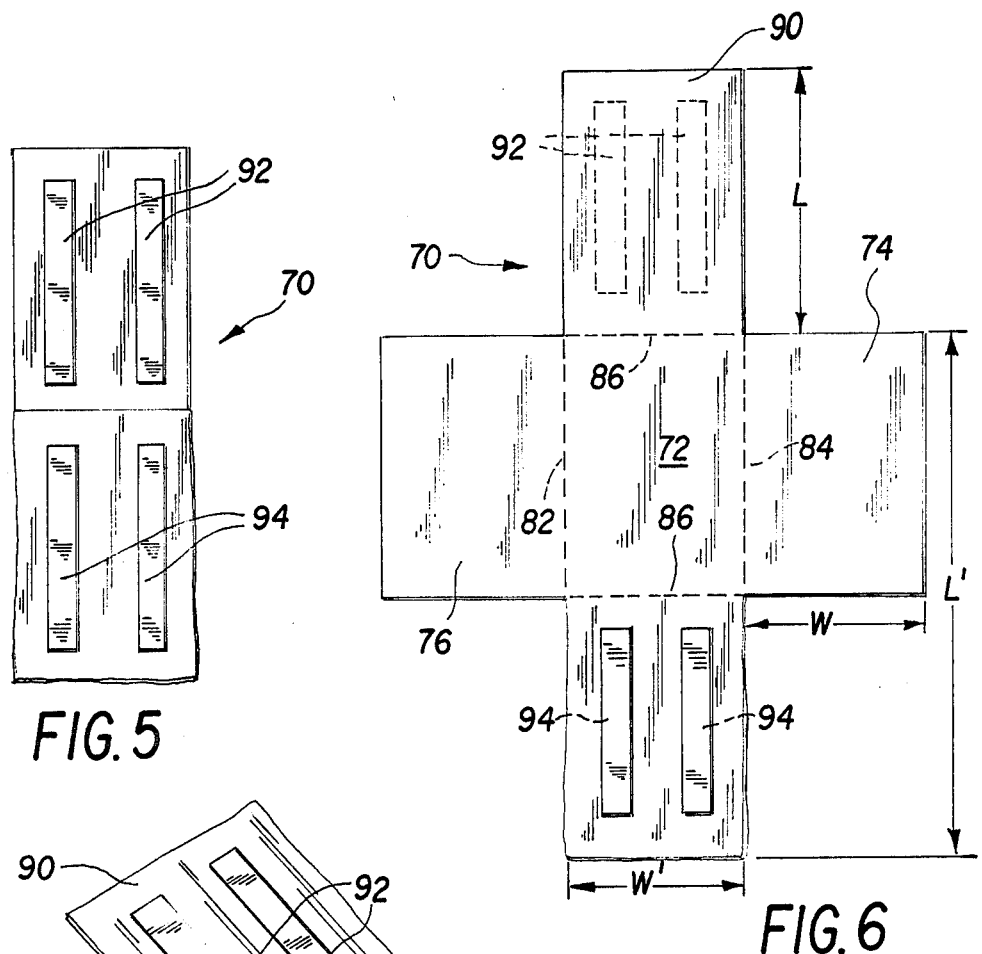
FIG. 5
FIG. 6
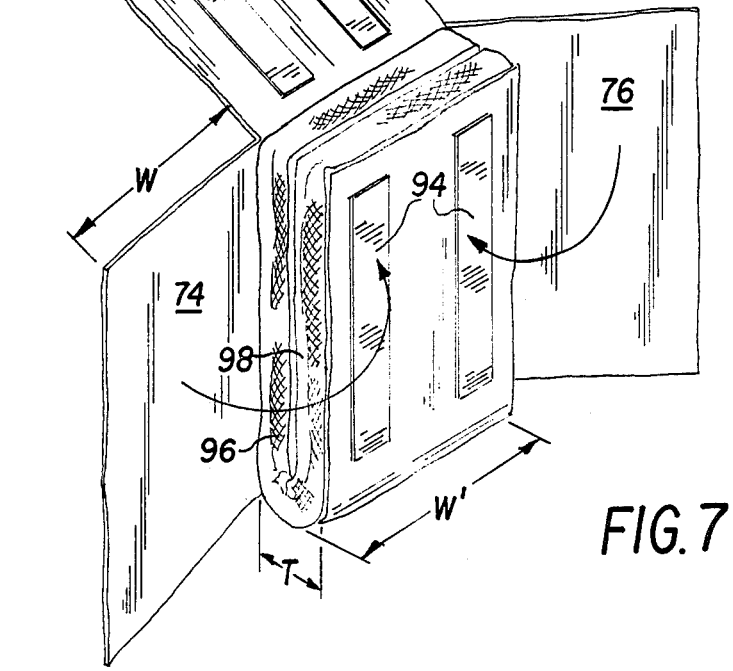
FIG. 7

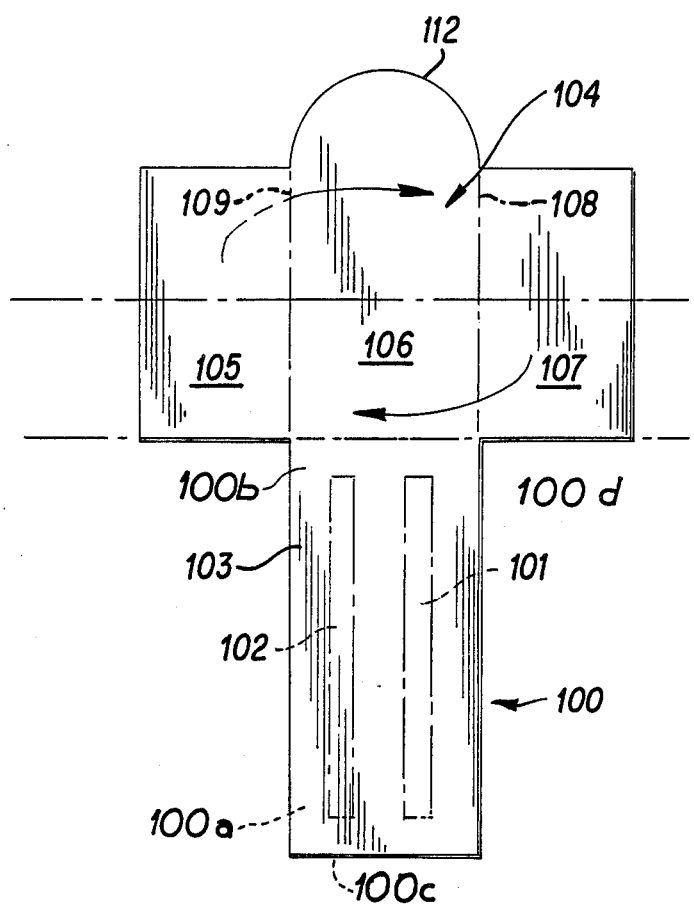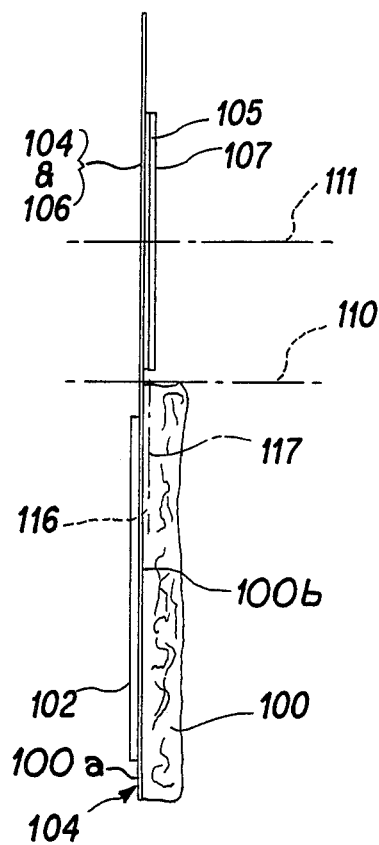
FIG. 8　　FIG. 9
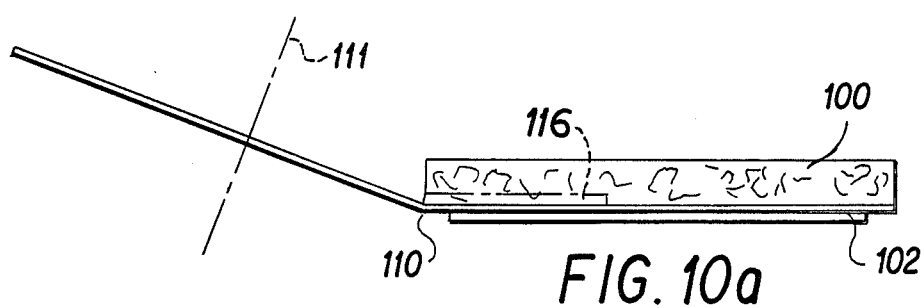
FIG. 10a
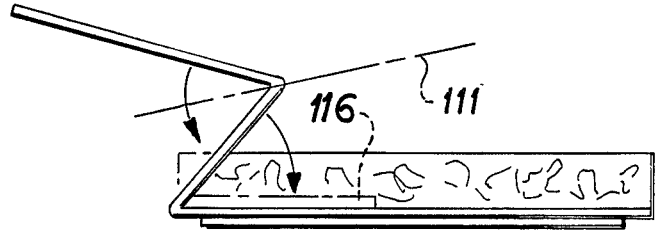
FIG. 10b

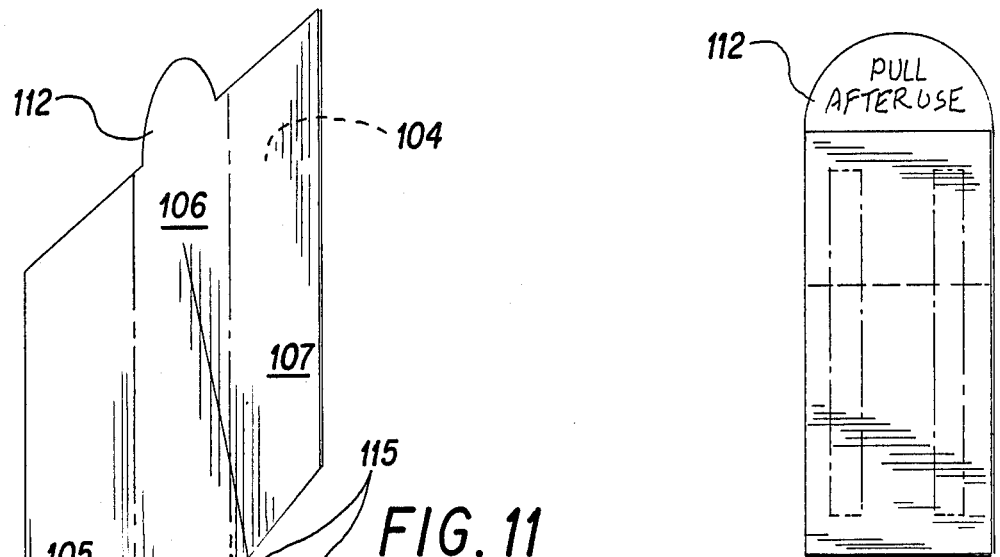
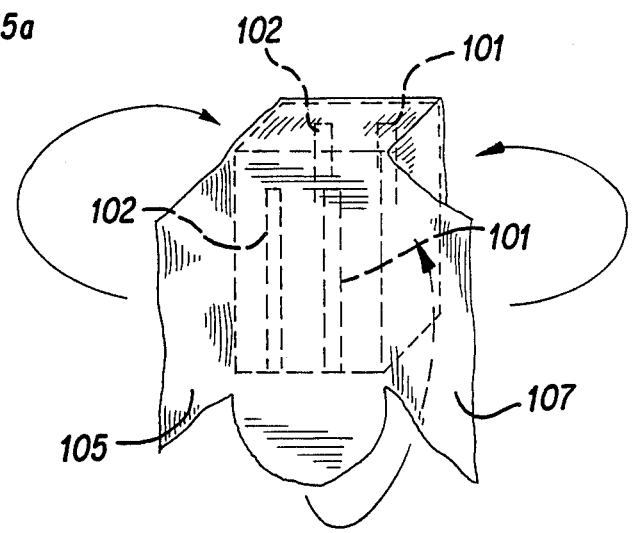
FIG. 10c
FIG. 11
FIG. 10d
FIG. 12

FEMININE PAD WITH ATTACHED DISPOSAL WRAP

BACKGROUND OF THE INVENTION

Field of the Invention

The invention relates to absorbent napkins, feminine pads and the like, and further, the invention relates to a pad including an infolding wrap or an infolding panel for adapting the assembly for ultimate disposal thereof and its manufacture, and more particularly the invention is directed to an absorbent napkin with infolding panel consisting of an absorbent pad of elongated rectangular configuration with elongate edges defining a short and long dimension and having a body face and an outer face for engagement to clothing, a wrap member attached to at least one of the several elongated edges and adapted to fold along one of the elongate edges of the member to inwrap the body face, a fold line or section positioned transversely about a mid-portion of the pad for infoldment of the body face along the fold section thereof, and an adhesive member secured transversely of the wrap means for adhesive engagement to the clothing. The dimensions of the wrap member along the long dimension are half-lengths of the long dimension of the absorbent pad.

The invention in its more preferred embodiment relates to a feminine pad having a self-contained wrap to be used for convenient and considerate disposal of a used pad and which secondarily utilizes the adhesive strips normally used for the placement security of the pad during use as a means to secure the wrapper about a half-folded pad in preparation for its disposal. The pad thus provides a self-contained means to wrap the used absorbent feminine pad for use with an infolding wrap consisting of an elongated absorbent pad with long edges and short edges and defining a short and long dimension and having a body face and an outer face for engagement with undergarment clothing, the elongated absorbent pad being adapted variously to half-fold upon itself, and means included in the elongated absorbent pad providing a desirability by a user after removal of the elongated absorbent pad from the undergarment clothing to generally intuitively half-fold the body face of the elongated absorbent pad upon itself, such that in no way is there any inhibition of the desirability of the user to not assert or pursue an immediate and generally intuitive step of half-infolding the pad as a first step after removal from the undergarment clothing.

The invention relates further to a device providing for the construction of an absorbent pad which provides by its infoldment for a discrete and convenient device for disposal after its use and to provide a convenient and appropriate package therefor and the manufacture thereof as more particularly described herein.

Description of the prior art

Various prior art types of absorbent napkins, feminine pads, bandage pads and pads provided for covering wounds, and the like, as well as apparatus and their construction in general, are found to be known, but there are no multi-function constructions of absorbent napkins, feminine pads, bandage pads and pads provided for covering wounds that provided for integral features allowing infolding thereof or inwrapment in itself for availing a discreet disposition of used or soiled ones thereof.

Some types of self-contained covering are seen provided in the prior art but are generally all found unsatisfactory where a convenience and a consideration are provided for requiring that the napkin need be generally provided with a defined characteristic of intuitively half-folding a used pad as an important first requirement after removal of the pad from the undergarment.

Brooks U.S. Pat. No. 3,963,029 shows a diaper package having free ends provided to secure a used diaper in a rolled configuration.

Elmore U.S. Pat. No. 3,035,578 discloses sanitary napking cover having a removable sheet of liquid repellant material which is removably attached by means of a tear string.

Norris U.S. Pat. No. 4,417,894 shows a towelsheet disposable diaper having a sheet removably associated with a disposable diaper.

Srinivasen et al U.S. Pat. No. 3,973,567 teaches use of a wrapped sanitary napkin with its wrapper sheet of flexible material which protects the napkin and its adhesive element before use and is utilized during disposal of the napkin after its use. The sheet is releasably held in place by the adhesive element. It suggests that during use the sheet is pulled away and stored in the user's purse.

Baum U.S. Pat. No. 4,402,689 discloses a sanitary napkin having one or two resin fixed wrapper panels with adhesive for affixing the napkin to the undergarment during use and then for attaching the wrapper panels over the used body face prior to half-folding. This seems inappropriate because the free surface energy between the moistened pad and the adhesive strips of the wrapper flaps is reduced causing a low interfacial tension between the adhesive strips and the moistened body surface. The result is a generally non-adhesive condition in accordance with:

$$Ws1 = gs + g1 - gs1$$

where:
Ws1 is the work of adhesion between a solid and liquid; and
$gs + g1 - gs1$ are surface free energies.

This application is an improvement over our application Ser. No. 06/758,756 filed July 25, 1985, now abandoned. This application considered such results and its departure over the prior art was providing an end sealing flap that adhesively holds the folded free ends. However, this feature was only as effective as the adhesive ability of the wrapper flaps to the used body surface that has been shown to negligible. The problem is compounded due to the compression of a feminine pad during use resulting in a flat surface being found unavailable to accept the wrapper flaps.

There are suggestions found in prior art absorbent pads that provide certain features in utility in feminine pads that have attached disposal flaps with adhesive strips to provide placement security during use and are used to wrap a used pad in preparation for disposal. Further, the application teaches that the sealing flaps are secured in the disposal configuration by a second use of the adhesive strips that initially provide placement security during use. User test results show complaints and criticism of slipage and placement security. To eliminate this criticism the normally floated wrapper flaps were made substantially stationary by detachably affixing with resin the flaps to the outer face thereof and thence similarly attaching a flap to the combination resin. The resin fastening procedure eliminated the in-place slippage but created a subsequent disadvantage. It had been the object of the invention, had not the in-place security concern developed, that upon removal of a used pad from the undergarment, immediate and simple fold-overs of these flaps would precede the half-folding used by the pad. This would be followed by the placement of the end closure flap. However the resin secured flaps made a very awkward circumstance in that a flap separation step was introduced. Summarily by affixing the wrapper panels with resin, the immediate placement of the wrapper panels over the used body face prior to half-folding the used pad became undesirably awkward. Short-comings of these features are overcome by altering the full pad length wrapper to half-lengths.

Such known prior uses teach and disclose various types of absorbent napkins, feminine pads and bandage pads of sorts and of various manufacturers and the like as well as methods of their construction, but none of them whether taken singly or in combination disclose the specific details of the combination of the invention in such a way as to bear upon the claims of the present invention.

SUMMARY OF THE INVENTION

An object, advantage and feature of the invention is to provide an absorbent napkin or pad structure which provides a discrete and convenient arrangement for its appropriate disposal after use.

Another object of the invention is directed further to a device providing for an absorbent pad that is integral therewith and in which the disposal wrap is virtually discreet for disposal.

An object of a preferred feature of the invention is to provide an absorbent feminine napkin for use with an infolding wrap having an elongated absorbent pad with long edges and short edges and defining a short and long dimension and having a body face and an outer face for engagement with undergarment clothing, allowing the elongated used absorbent pad to be adapted variously to first half-fold upon itself, and included in the elongated absorbent pad, and intuitively providing a desirability by a user after removal of the elongated absorbent pad from the undergarment clothing to generally and intuitively half-fold the body face of the elongated absorbent pad upon itself prior to wrapping for disposal.

It is an object of the invention to overcome objections of prior art methods of constructions and the structures known and found in there, by here providing a feminine pad having a self-contained wrapper member that in no way comprises but may augment the user's first and intuitive step to half-infold a used pad prior to wrapping for disposal.

It is a further object of the invention to provide a wrapper member as constructed and arranged that does not reduce any efficacy of in-place security during use.

These together with other objects and advantages which will become subsequently apparent reside in the details of the process and operation thereof as more fully hereinafter is described and claimed, reference being had to the accompanying drawings forming a part hereof, wherein like numerals refer to like parts throughout.

DESCRIPTION OF THE SEVERAL VIEWS OF THE DRAWINGS

FIG. 5 is a plan view of a large size absorbent pad according to another embodiment of the present invention.

FIG. 6 is a plan view of a large size absorbent pad in an open position showing an outer face with flaps in unfolded relation, and FIG. 7 is a generally perspective view showing completed steps of folding of the sealing flaps of the large size absorbent pad.

FIG. 8 is a view of an embodiment of the invention and showing an outer view of a pad according to a preferred embodiment and best mode of the present invention.

FIG. 9 is a side view thereof.

FIGS. 10a, 10b, 10c and 10d are showings of operative steps of the folding of the panels thereof, and FIGS. 11 and 12 are a perspective views of the arrangement of the feminine pad.

It should be observed at this point that the term 'body face' used herein will refer to that side of the pad that is to be worn facing one's body surface and the term outer face refers to that side of the pad that attaches by an adhesive member to the proximate surface of the clothing of the undergarment. Further, FIGS. 1 through 4 show absorbent pads generally classified as 'mini' pads or 'shields' and may possess no, or a small, substantial thickness dimension that would influence the covering ability of the required length of the closure and wrapper flaps. FIGS. 5 through 7 disclose the wrapper flap features for those absorbent pads that are generally classified as 'maxi' or 'super' and they not only have their own substantial thicknes dimension but also have an excessive thickness at a half-fold location as described more particularly below.

DESCRIPTION OF A PREFERRED EMBODIMENT OF THE INVENTION

Figure 1:
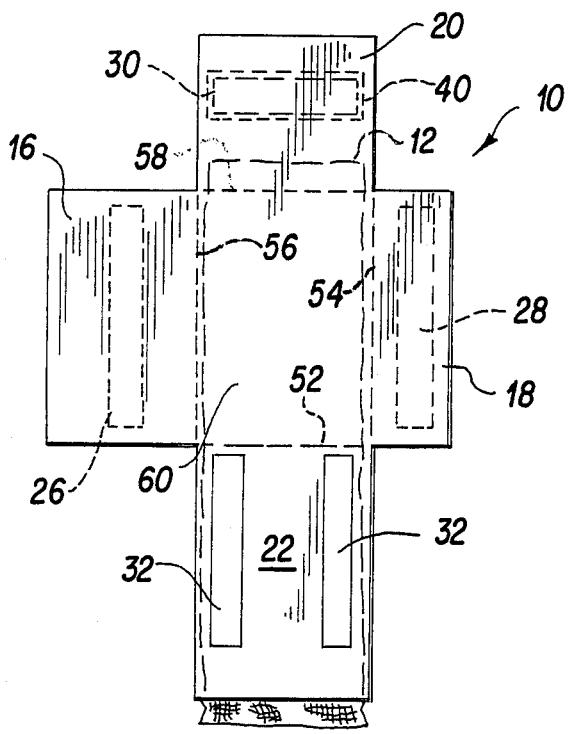
FIG. 1 is a plan view of an absorbent pad in an open position showing an outer face with flaps in unfolded relation and illustrating a typical installation of the absorbent pad of the present invention.

Referring now to the drawings there is shown in FIG. 1 a bandage pad, feminine napkin or absorbent pad 10 in an open position showing an outer face with flaps in unfolded relation and in which the pad is constructed of a gauze, fabric or cloth material 12 or other suitable absorbent material. The absorbent pad 10 is shown to possess a central panel with wrapper panels 16, 18 and a closure panel 20 and a one piece outer liner 22. Closure adhesive strip 30 possesses an individual protective strip 40. Adhesive strips 26, 28 and adhesive strip 30 for the closure panel 20 are shown in phantom in FIG. 1.

Adhesive strips 32 are formed as in integral part of the absorbent pad 10.

Figure 2:
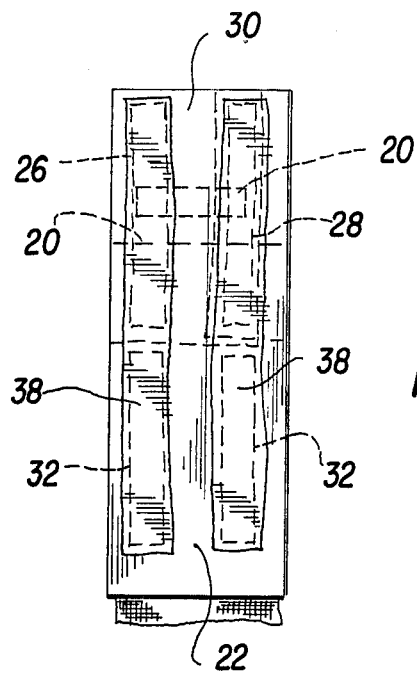
FIG. 2 is a plan view of the outer face of a typical absorbent pad with flaps in a folded position packaged prior to use and embodying the concepts of the invention.
Figure 2A:
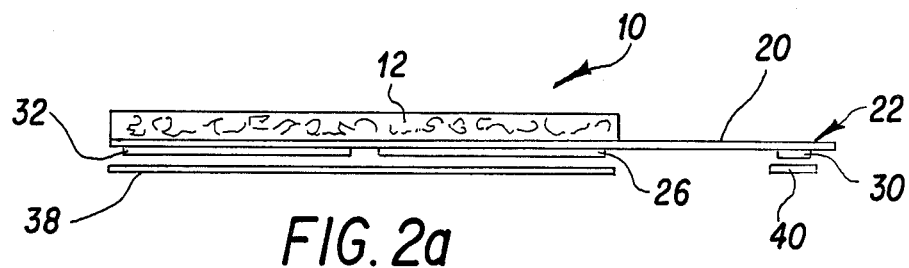
FIG. 2a is a side view of the absorbent pad of FIG. 2.
Figure 2B:
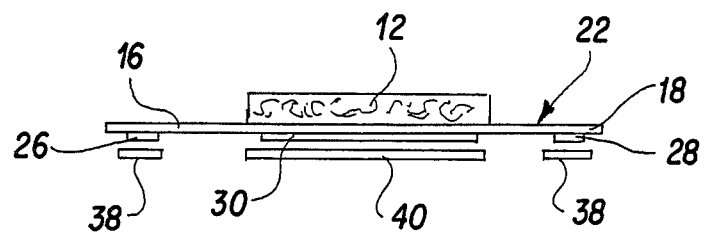
FIG. 2b is a front view of the absorbent pad of FIG. 2.

FIG. 2 shows the outer face of a packaged typical mini absorbent pad 10 prior to use and further showing a single protective covering 38 for each pair of adhesive strips 26, 28, 30, 32. The absorbent pad 10 in FIGS. 2a and 2b show open panels and the outer liner 22 is formed integrally with the body of material 12, panel 14 and outer liner 22. Adhesive strips 26, 28 on the wrapper panel 16, 18 and pad adhesive strips 32 are constructed in a split pair configuratin while an adhesive strip protective covering 38 shown detached is of single construction for each pair of adhesive strips 26, 28, 32.

Figure 3:
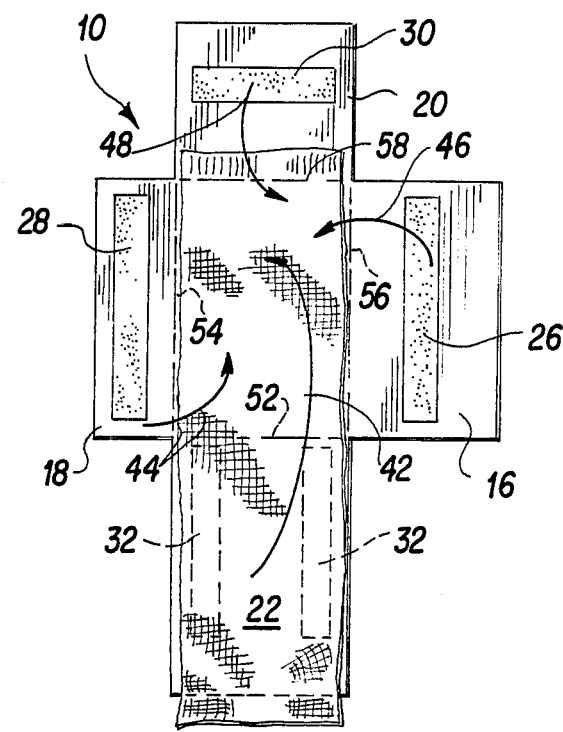
FIG. 3 is a bottom view of FIG. 2 and showing the absorbent pad as worn facing the body, known as the body face.

The embodiment shown in FIG. 3 shows the outer or body side of FIGS. 1 and 2 as the absorbent pad 10 is being prepared for its disposal after use. The absorbent pad 10 first is half-folded along line 52 shown by arrow 42 and then followed by wrapper flap fold lines 54, 56 shown by arrows 44, 46 and followed then in a step to end-seal the absorbent pad 10 by folding the closure flap 20 along line 58 shown by arrow 48. The sequence of folding wrapper flaps or panels 16 18 is relatively unimportant since one panel 18 is equivalent to one-half the pad width while the other wrapper panel 16 is equivalent to three-quarters of the width of the absorbent pad 10, thus insuring adequate overlap when the thickness of a half-folded maxi absorbent pad 10 is considered.

Figure 4:
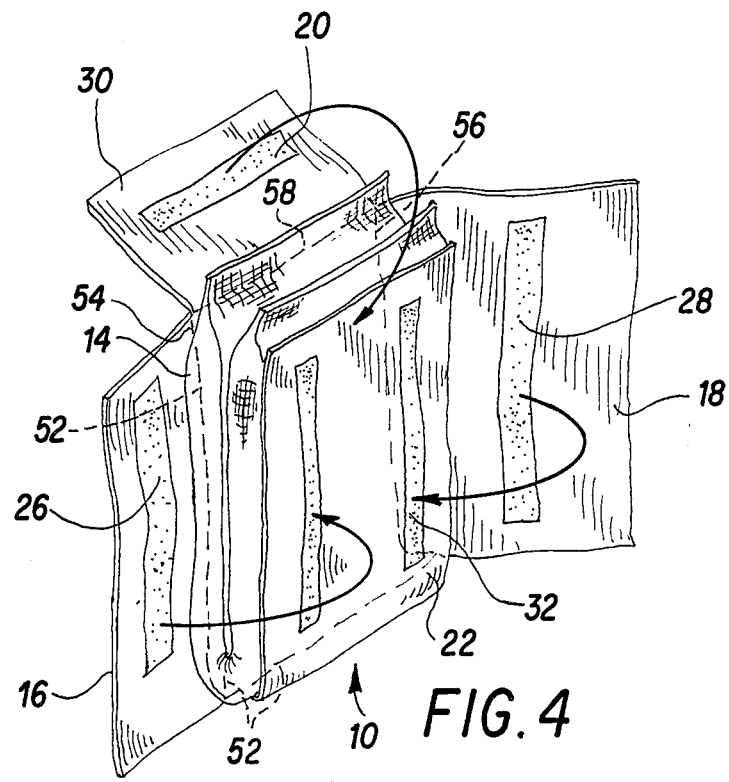
FIG. 4 is a generally perspective view showing completed steps of folding of the sealing flaps of the absorbent pad.

FIG. 4 shows an advanced sequence of the folding procedure and ultimately, the sealing panels 16, 18, 20 will be secured with either four single or two double attachment points that formed the pre-use package. Also shown in FIG. 4 is the concept that the folded radius or turns about the fold lines 52, 54, 56, 58 of the absorbent pad 10 will be completely infolded or inwrapped and in which the original absorbent pad 10 is adequately covered within a thin elastomeric coated material or plastic coated material 60 provided exterior of the absorbent pad 10.

FIG. 5 shows a package embodying an outer face of the absorbent pad 70 identified as a super or maxi type of construction of the invention, that is, one that has relatively substantial thickness over that embodiment of FIGS. 1 through 4 and in which the adhesive protective covering is not shown. FIG. 6 shows an outer face 72 of the unfolded absorbent pad 70. The width of wrapper panels 74, 76 along the fold lines 82, 84 are such as to nearly approximate the width of the absorbent pad 70 and are without adhesive strips as shown. Closure panel 90 is shown to have a length that nearly approximates one-half the length of the absorbent pad 70. Double adhesive strips 92 are longitudinally oriented on closure panel flap 90 to provide attachment security in combination with pad double adhesive strips 94.

FIG. 7 shows like FIG. 4 steps of folding-wrapping in advance sequences of closing or infolding the absorbent pad 70. Again the width of wrapper panel 74 is sufficient to cover the double edge surface thickness of the folds 96, 98 and seal upon a closer one of the adhesive strips 94 and extend beyond the mid-point of the absorbent pad 70 shown by fold lines 82, 84. Similarly, wrapper panel 76 will seal upon another one of the adhesive strips 94 and overlap in-place with the wrapper panel 74. Closure panel 90 is then folded over the ends of the absorbent pad 70 and providing thereby a completely sealed absorbent pad 70 ready for disposal.

In preparing the manufacture of the absorbent pad in package form the wrapper panels or flaps 74, 76 and closure panel or flap 90 are spot resinadhered onto the other and both to the outer liner surface of the absorbent pad 70 to provide placement security during use.

FIGS. 8–12 show a preferred embodiment and generally best mode of the invention. FIG. 8 illustrates an elongated cover sheet or layer 103, preferably of absorbent composition, with an inner face 100b, and having an outer layer or face 100a of a moisture-impermeable plastic composition. The cover sheet 103 is provided with opposite end portions 100c, 100d. An absorbent pad 100 is suitably affixed to the inner face 100b while adhesive means, in the form of a plurality of longitudinally extending strips 101, 102, are attached to the outer face 100a. During use of the napkin, the adhesive strips 101, 102 will be understood initially to serve the purpose of securing the napkin to the crotch of an undergarment (not shown). A disposal wrap 104, including a central, intermediate panel 106 and two lateral panels 105, 107, essentially comprises an uninterrupted continuation of the cover sheet 103, with the central panel 106 extending from the cover sheet end portion 100d. Panels 105 and 107 are alternately folded onto the central panel 106 along fold lines 108, 109 respectively, thusly forming a three panel extension of absorbent outer sheet 103. Fold lines 108, 109 are disposed toward the surface of the outer face 100a.

FIG. 9 shows a side view of the pad 100 with the disposal wrap 104 being alternately folded as shown in FIG. 8 and is seen as being prepared for further folding as shown in sequential set of FIGS. 10a, 10b, and 10c. In FIG. 10a, a triple layer is provided by sequentially folding the panels 105 and 107 onto the intermediate, central panel 106 and then is applied a step of accordion-folding of the panels 105, 106, 107 as shown and illustrated in FIG. 10b, whereupon the total thickness of the final pre-use configuration of the wrapper panels is 0.003 inches which is generally considered negligible bulk.

The folded panels 105, 107 of FIG. 10b on the panel 106 are then accordion-folded along the folded lines 110, 111 in the sequence and manner illustrated.

The disposal wrap 104 is prepared in the folded configuration prior to attachment to the longitudinal and bottom edges of the body surface covering, all of which are constructed to house the absorbent layer, by efficient manufacturing practices, methods and procedures. Attaching these two coverings results in construction of an envelope 116 in FIG. 9 from which the folded wrap 104 is extracted in preparation for wrapping as a used pad.

Envelope 116 is shown exaggerated in its depth dimension for purposes of clarity in FIGS. 9, 10a, 10b, 10c. The 0.003 inch thickness of the folded wrapper results in the outer pad surface 104 of FIGS. 8 and 9 being essentially planar with no added bulk.

FIGS. 10c and 10d show a prior-to use pad having tab 112 disposed as an extension of panel 106 and the sheet 103 and is shown appropriately labelled with printed indicia or printing in general, for example, 'PULL AFTER USE', and as well as by other means, augments providing a desirability of a user after removal of the elongated absorbent pad from the undergarment clothing to generally and intuitively half-infold the pad along the body face of the elongated absorbent pad upon itself. In preparation for disposal the pad is generally half-folded and the pulling of tab 112 results in the wrapper 104 becoming available as shown in FIG. 11 for complete encirclement about the pad. Tab 112 may be of a rectangular or rounded construction.

With further reference to FIG. 11, the wrapper 104 in its entirety, is folded over the juxtaposed used free ends 115 and the tab 112 is folded over the fold or radius 115a. The panel 106 and the tab 112 are held secure by a secondary use of the adhesive strips 101, 102. The panels 105, 107 are then folded around the edges of the pad as shown in FIG. 12 and are secured by the secondary use of the remaining exposed portions of the adhesive strips 101, 102. The panels 105, 107 are generally dimensioned to be as wide as the pad itself and will generally always result in an overlap condition when utilized in the disposal configuration. Thusly, all surfaces of the used pad are enveloped within the wrapper itself.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention.

What is claimed and desired to be secured by Letters patent is:

1. A feminine napkin comprising;
   an elongated absorbent pad provided with a body surface and an outer surface and having opposite free ends,
   an elongated cover sheet having an inner face juxtaposed said pad outer surface and provided with an opposite outer face, said cover sheet including opposite end portions substantially underlying said pad free ends,
   adhesive means in said cover sheet outer face intermediate said opposite end portions,
   a disposal wrap sheet extending from one said cover sheet end portion, and
   said wrap sheet including a plurality of laterally adjacent panels foldable to a before-use position opposed to and underlying said pad outer surface, whereby
   following use, said pad is half-foldable upon itself with portions of said body surface juxtaposed one another and said wrap sheet is displaceable from said before-use position with said panels then unfoldable and movable to a position wherein subsequent re-folding of said panels substantially fully envelopes said pad outer surface within said wrap sheet with said adhesive means engaging and retaining said panels in an after-use position.

2. A feminine napkin according to claim 1 wherein, said cover sheet and wrap sheet are integral and together define, when said wrap sheet is unfolded, a substantially T-shaped configuration.

3. A feminine napkin according to claim 1 wherein, said wrap sheet panels include a pair of outer, lateral panels bounding a central intermediate panel.

4. A feminine napkin according to claim 1 wherein, said adhesive means includes an adhesive strip.

5. A feminine napkin according to claim 1 wherein, said wrap sheet is foldable along a transverse line to provide a Z-fold when in said before-use position.

6. A feminine napkin according to claim 1 wherein, said adhesive means are adapted to initially engage the crotch of an undergarment during use of the napkin.

7. A feminine napkin according to claim 1 wherein, following use, said pad and cover sheet are transversely foldable in half to juxtaposition equal portions of said pad body surface.

8. A feminine napkin according to claim 1 including, a pull tab extending from said wrap sheet, and said pull tab projecting beyond one said pad free end when said wrap sheet is folded in said before-use position.

9. A feminine napkin according to claim 3 wherein, said central panel is of a width substantially equal to that of said cover sheet and pad.

10. A feminine napkin according to claim 3 wherein, said central and outer panels define a longitudinal extent greater than one-half the longitudinal extent of said pad.

11. A feminine napkin according to claim 4 including, a pair of said strips each extending longitudinally of said cover sheet.

* * * * *